US012575937B2

(12) United States Patent
Schwartz et al.

(10) Patent No.: US 12,575,937 B2
(45) Date of Patent: Mar. 17, 2026

(54) TOE IMPLANT, RELATED KIT, SURGICAL METHOD, AND METHOD OF MANUFACTURING

(71) Applicant: BIOPOLY, LLC, Fort Wayne, IN (US)

(72) Inventors: Herbert E. Schwartz, Fort Wayne, IN (US); Matthew L. Mroczkowski, Fort Wayne, IN (US); Stone Miguel, Fort Wayne, IN (US)

(73) Assignee: BioPoly, LLC, Fort Wayne, IN (US)

( * ) Notice: Subject to any disclaimer, the term of this patent is extended or adjusted under 35 U.S.C. 154(b) by 883 days.

(21) Appl. No.: 17/813,201

(22) Filed: Jul. 18, 2022

(65) Prior Publication Data

US 2022/0346965 A1      Nov. 3, 2022

Related U.S. Application Data

(63) Continuation of application No. PCT/US2021/013905, filed on Jan. 19, 2021.

(60) Provisional application No. 62/963,240, filed on Jan. 20, 2020.

(51) Int. Cl.
        *A61F 2/42*         (2006.01)
        *A61L 27/56*        (2006.01)
        *A61F 2/30*         (2006.01)

(52) U.S. Cl.
        CPC ............ *A61F 2/4225* (2013.01); *A61L 27/56* (2013.01); *A61F 2002/30622* (2013.01); *A61F 2002/4233* (2013.01)

(58) Field of Classification Search
        CPC ...... A61F 2002/4233; A61F 2002/4238; A61F 2/4225; A61F 2002/4228; A61F 2002/30205; A61F 2002/3021; A61F 2002/30227; A61F 2002/30011; A61F 2002/3092; A61F 2/4606; A61F 2002/2839
        See application file for complete search history.

(56) References Cited

U.S. PATENT DOCUMENTS

| | | | |
|---|---|---|---|
| 8,303,664 | B1 | 11/2012 | Burstein et al. |
| 9,044,332 | B2 | 6/2015 | Goswami et al. |
| 10,307,257 | B2 | 6/2019 | Grotz |
| 2003/0083433 | A1 | 5/2003 | James et al. |
| 2005/0112397 | A1 | 5/2005 | Rolfe et al. |
| 2007/0078518 | A1 | 4/2007 | Lavi |

(Continued)

FOREIGN PATENT DOCUMENTS

| | | |
|---|---|---|
| EP | 1096906 | 7/1999 |
| JP | 2014506177 | 3/2015 |

OTHER PUBLICATIONS

Arthosurface Pamphlet, Franklin, MA, 16 pages.

(Continued)

*Primary Examiner* — Javier G Blanco
(74) *Attorney, Agent, or Firm* — Heslin Rothenberg Farley & Mesiti P.C.

(57)           ABSTRACT

Disclosed herein is a toe implant for replacing a portion of a human toe joint, as well as a related kit, surgical method, and method of manufacturing. Specifically, the toe implant may include a bearing member having a curved interface surface and a fixation member coupled to the bearing member. The fixation member may include a first portion having a non-porous barrier, and a tapered second portion.

5 Claims, 20 Drawing Sheets

(56) References Cited

U.S. PATENT DOCUMENTS

| | | |
|---|---|---|
| 2009/0240337 A1 | 9/2009 | Myung et al. |
| 2011/0153028 A1* | 6/2011 | Albertorio .............. A61L 27/56 |
| | | 623/23.63 |
| 2011/0257753 A1 | 10/2011 | Gordon et al. |
| 2014/0039621 A1 | 2/2014 | Gordon et al. |
| 2014/0188244 A1 | 7/2014 | Thomas et al. |
| 2017/0367828 A1 | 12/2017 | Steines et al. |
| 2018/0036142 A1 | 2/2018 | Wahl et al. |

OTHER PUBLICATIONS

International Search Report and Written Opinion of the International Searching Authority for International Application No. PCT/US2021/013905 mailed on Apr. 1, 2021, 8 pages.

International Preliminary Report on Patentability for International Application No. PCT/US2021/013905 dated Jul. 26, 2022, 7 pages, International Bureau of WIPO.

* cited by examiner

200

270

272

250

400

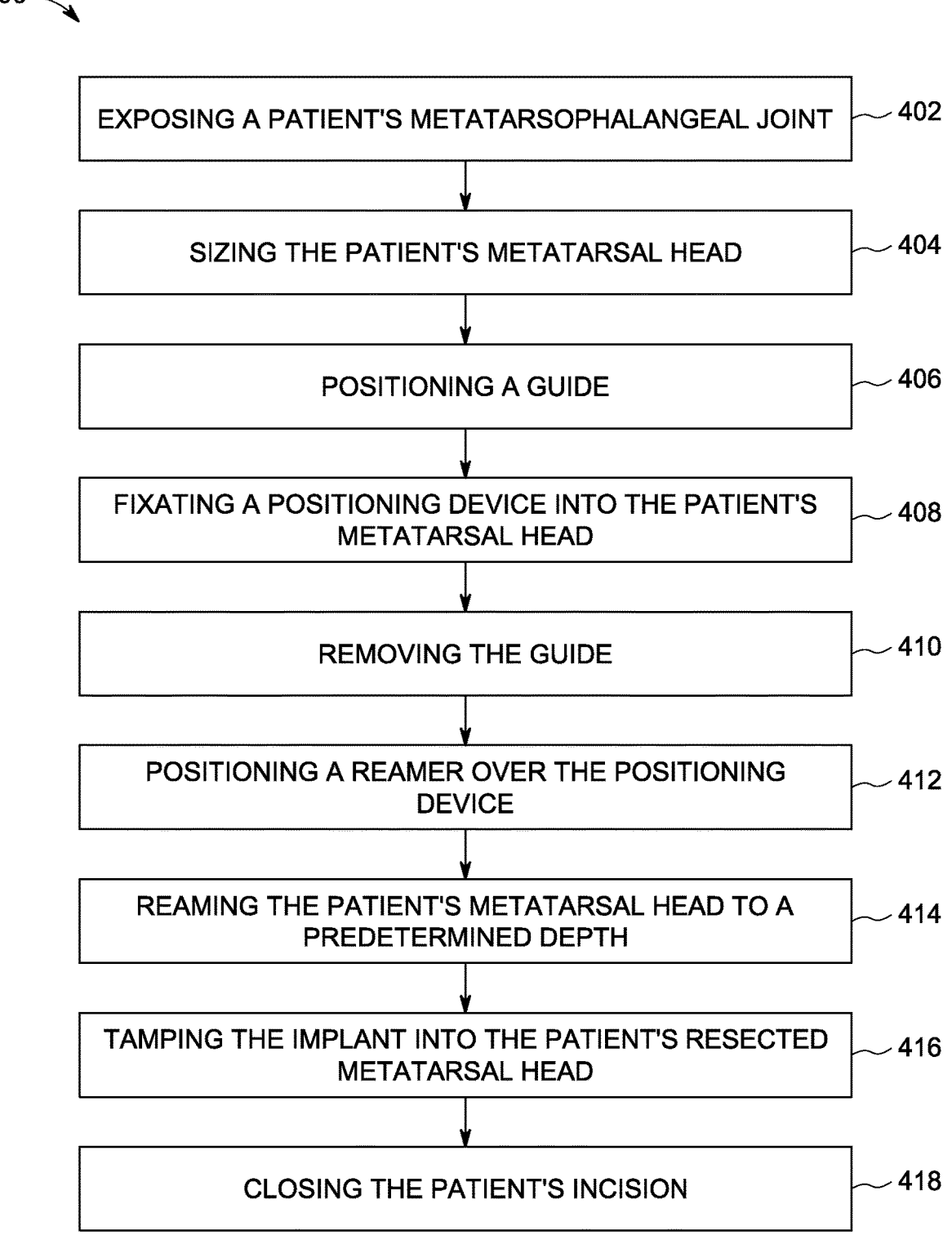

EXPOSING A PATIENT'S METATARSOPHALANGEAL JOINT ~ 402

SIZING THE PATIENT'S METATARSAL HEAD ~ 404

POSITIONING A GUIDE ~ 406

FIXATING A POSITIONING DEVICE INTO THE PATIENT'S METATARSAL HEAD ~ 408

REMOVING THE GUIDE ~ 410

POSITIONING A REAMER OVER THE POSITIONING DEVICE ~ 412

REAMING THE PATIENT'S METATARSAL HEAD TO A PREDETERMINED DEPTH ~ 414

TAMPING THE IMPLANT INTO THE PATIENT'S RESECTED METATARSAL HEAD ~ 416

CLOSING THE PATIENT'S INCISION ~ 418

TOE IMPLANT, RELATED KIT, SURGICAL METHOD, AND METHOD OF MANUFACTURING

CROSS REFERENCE TO RELATED APPLICATION

This application is a by-pass continuation of PCT International Application No. PCT/US2021/013905, filed Jan. 19, 2021, and entitled "A Toe Implant, Related Kit, Surgical Method, and Method of Manufacturing" which claims priority benefit under 35 U.S.C. § 119(e) of U.S. Provisional Application No. 62/963,240 filed Jan. 20, 2020 and entitled "A Toe Implant, Related Kit, Surgical Method, and Method of Manufacturing", which is incorporated herein by reference in its entirety.

TECHNICAL FIELD

The present disclosure relates generally to surgical implants for use in repairing a joint. More particularly, but not exclusively, the present invention relates to an implant for replacing a portion of a human toe joint and a related kit, surgical method, and method of manufacturing.

BACKGROUND

Active persons may put continuous stress on the first metatarsophalangeal (MTP) joint over time, which may eventually wear out the articular cartilage of the MTP joint and lead to the onset of arthritis. This condition, known as hallux rigidus, causes loss of movement and pain in the MTP joint. The MTP joint may also be damaged due to injury or genetic defects, which may cause deterioration and/or loss of the articular cartilage, thereby limiting a person's range of motion. In many situations, non-operative treatments may provide relief, but individuals with advanced stages of MTP cartilage damage may need surgery. Current surgical treatments for cartilage defects may include microfracture surgery, microdrilling techniques, osteoarticular transfer system (OATS) cartilage repair surgery, autologous chondrocyte implantation (ACI) or matrix-induced ACI (mACI), cheilectomy, MTP arthrodesis, MTP joint replacement (e.g., total or partial joint arthroplasty), and/or other techniques. However, some patients may not be good candidates for certain surgical techniques for various reasons (e.g., a patient's bone development stages, desired mobility, etc.). Additionally, existing implants used for treating damaged articular cartilage at the MTP joint may cause various unwanted side-effects including, but not limited to, failure due to shearing stress, loosening of the implant device, subsidence, fragmentation, fractures, breakage, misalignment, recurrence of deformity, limited joint motion, development of plantar keratosis, development of tenderness around the joint, development of long flexor tendonitis, development of metatarsalgia, and development of metallosis.

Therefore, a need exists for improved implant devices for use in treating articular cartilage damage of the MTP joint. In particular, there is a need for implant devices that enable a patient to maintain motion of the MTP joint while providing relief from symptoms associated with articular cartilage damage without unwanted side-effects.

SUMMARY

Shortcomings of the prior art are overcome, and additional advantages are provided through the provision, in one embodiment, of a toe implant that includes, for example, a bearing member having a curved interface surface. Further, the toe implant may include a fixation member coupled to the bearing member, where the fixation member includes a first portion having a non-porous barrier, and a tapered second portion.

Also provided herein is a kit that includes a toe implant. The kit may further include a guide that includes a trial toe implant, a shaft affixed to the trial toe implant and a guide engagement slot. The kit may also include a positioning device configured to engage the engagement slot of the guide. Further, the kit may include a reamer having at least one cutting flute and having a reamer engagement slot configured to engage the positioning device. The kit may also include a tamper for use in securing the toe implant.

In one aspect, a surgical method is provided. The surgical method includes exposing a patient's metatarsophalangeal joint, and sizing at least one of the patient's metatarsal distal head or phalangeal proximal head. A guide is positioned, and a positioning device is fixated into the at least one of the patient's metatarsal distal head or phalangeal proximal head via the guide's engagement slot. Further, the method includes removing the guide and positioning a reamer over the positioning device via the reamer's engagement slot. The at least one of the patient's metatarsal distal head or phalangeal proximal head is reamed to a predetermined depth, and the implant is tamped into the at least one of the patient's resected metatarsal distal head or phalangeal proximal head. The method also includes closing the patient's incision.

In another aspect, a method of manufacturing or fabrication is provided, which includes forming a fixation member and molding, via compression, a polymer onto a top portion of the fixation member.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

FIG. 19 is a flowchart of a surgical method, according to an embodiment of the present disclosure.

DETAILED DESCRIPTION

Figure 1A:
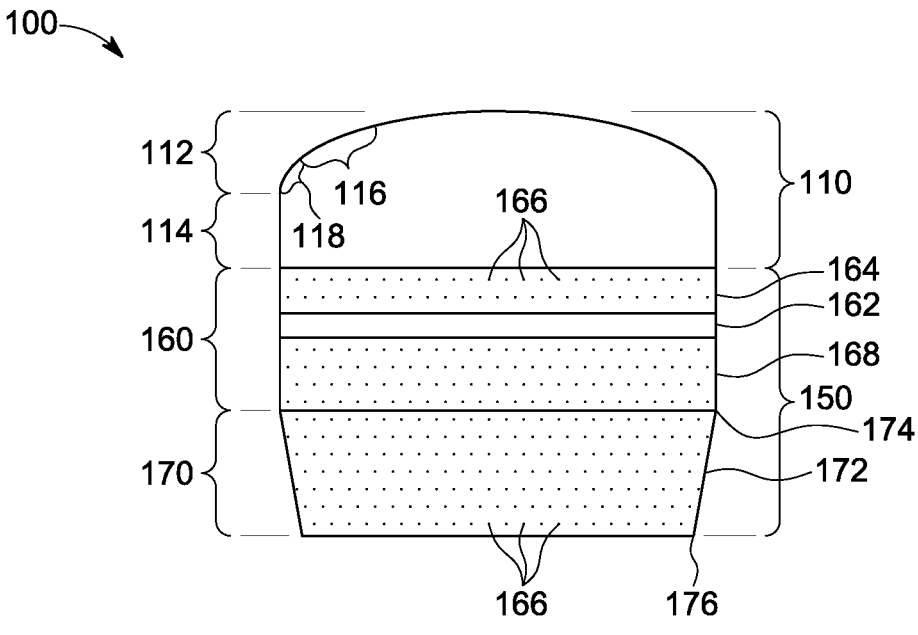
FIG. 1A is a side sectional view of an exemplary toe implant with a convex bearing member, according to an embodiment of the present disclosure.
Figure 1B:
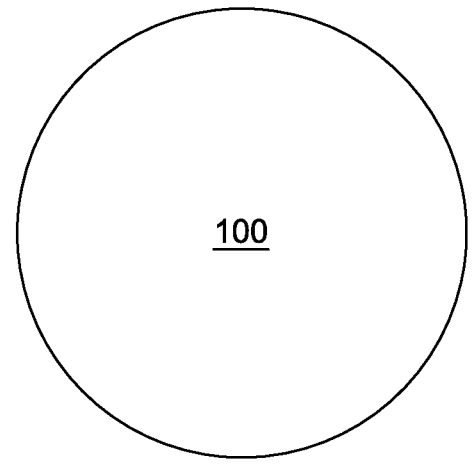
FIG. 1B is a top view of the exemplary toe implant of FIG. 1A, according to an embodiment of the present disclosure.
Figure 2A:
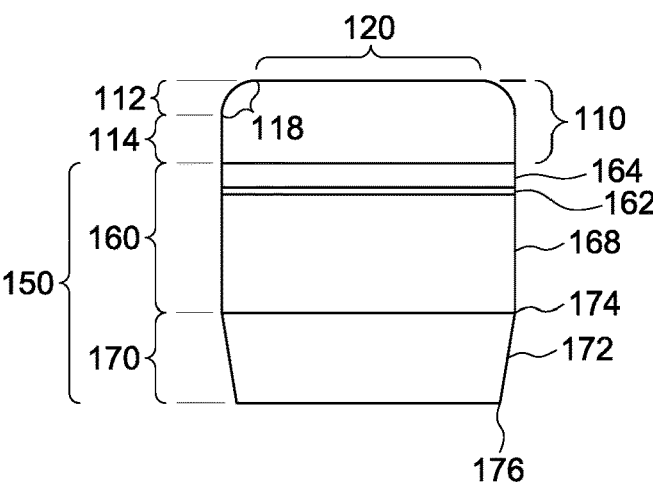
FIG. 2A is a side view of an exemplary toe implant with a concave bearing member, according to an embodiment of the present disclosure.
Figure 2B:
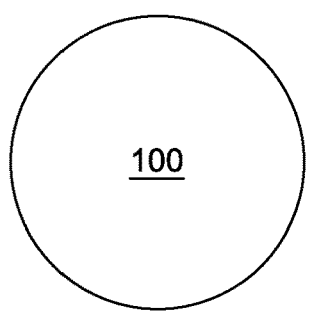
FIG. 2B is a top view of the exemplary toe implant of FIG. 2A, according to an embodiment of the present disclosure.
Figure 2C:
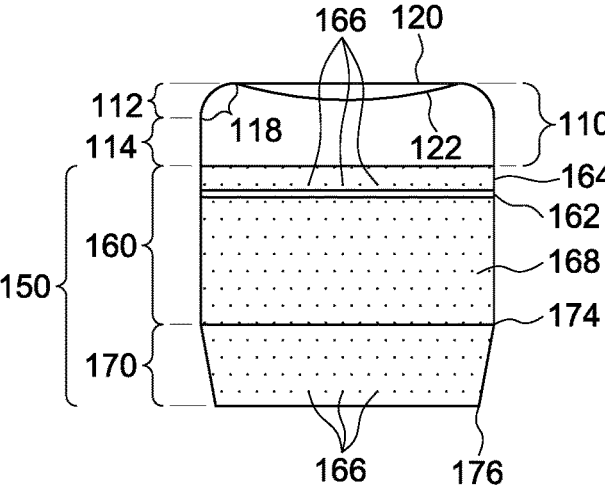
FIG. 2C is a side sectional view of an exemplary toe implant with a concave bearing member, according to an embodiment of the present disclosure.
Figure 3:
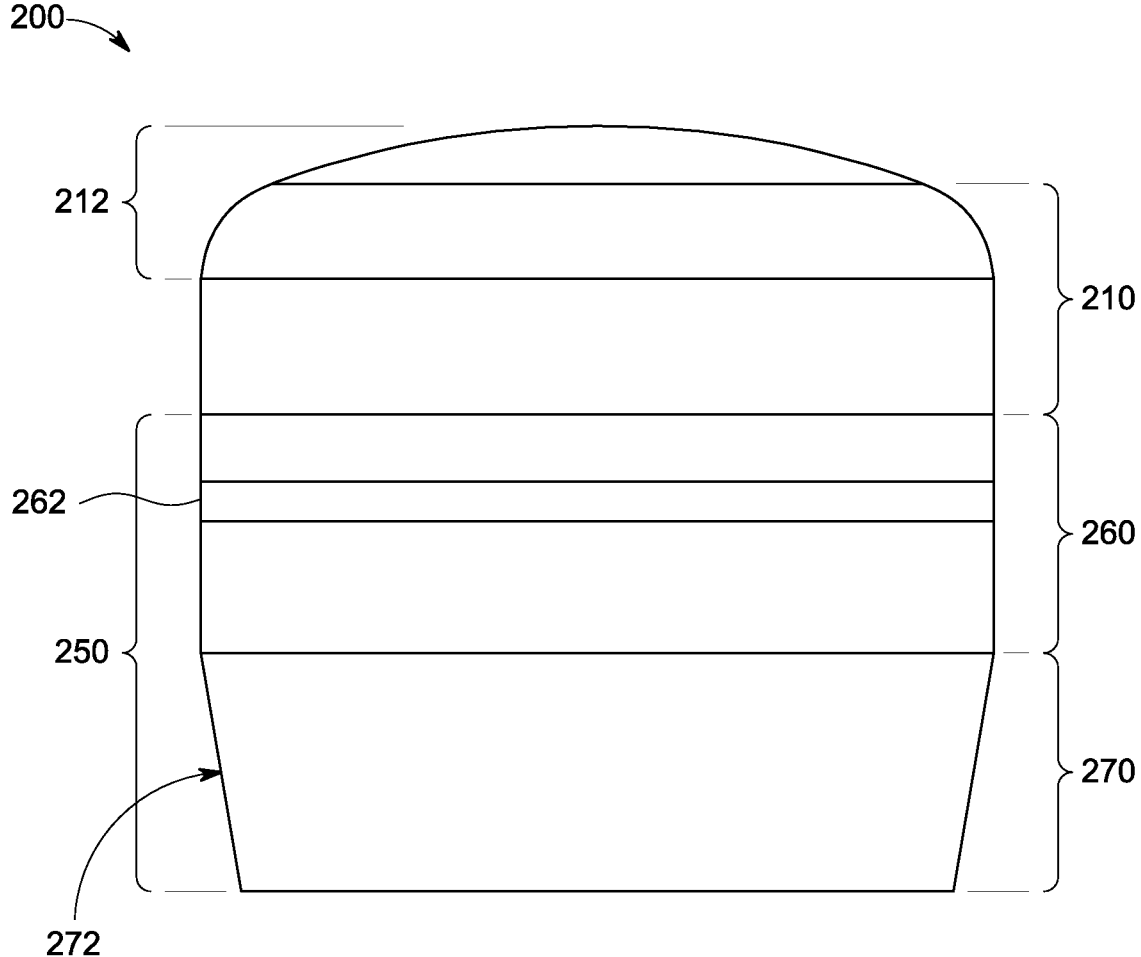
FIG. 3 is a side view of an exemplary toe implant with a convex bearing member, according to an embodiment of the present disclosure.
Figure 4:
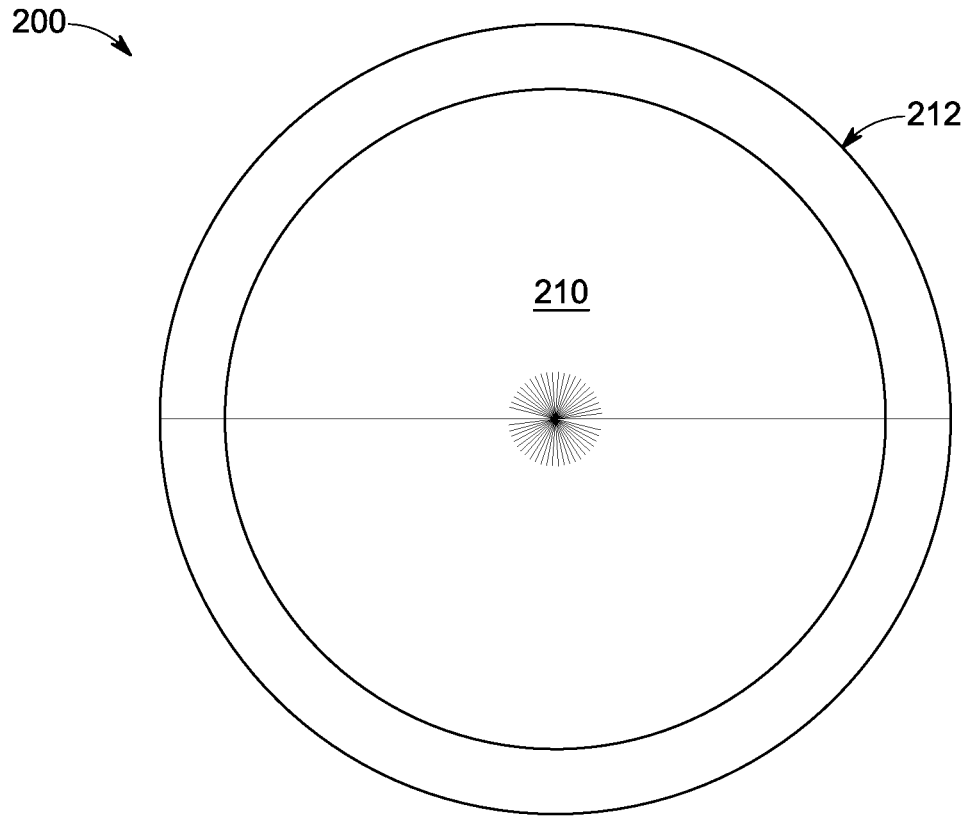
FIG. 4 is a top view of the toe implant of FIG. 3, according to an embodiment of the present disclosure.
Figure 5:
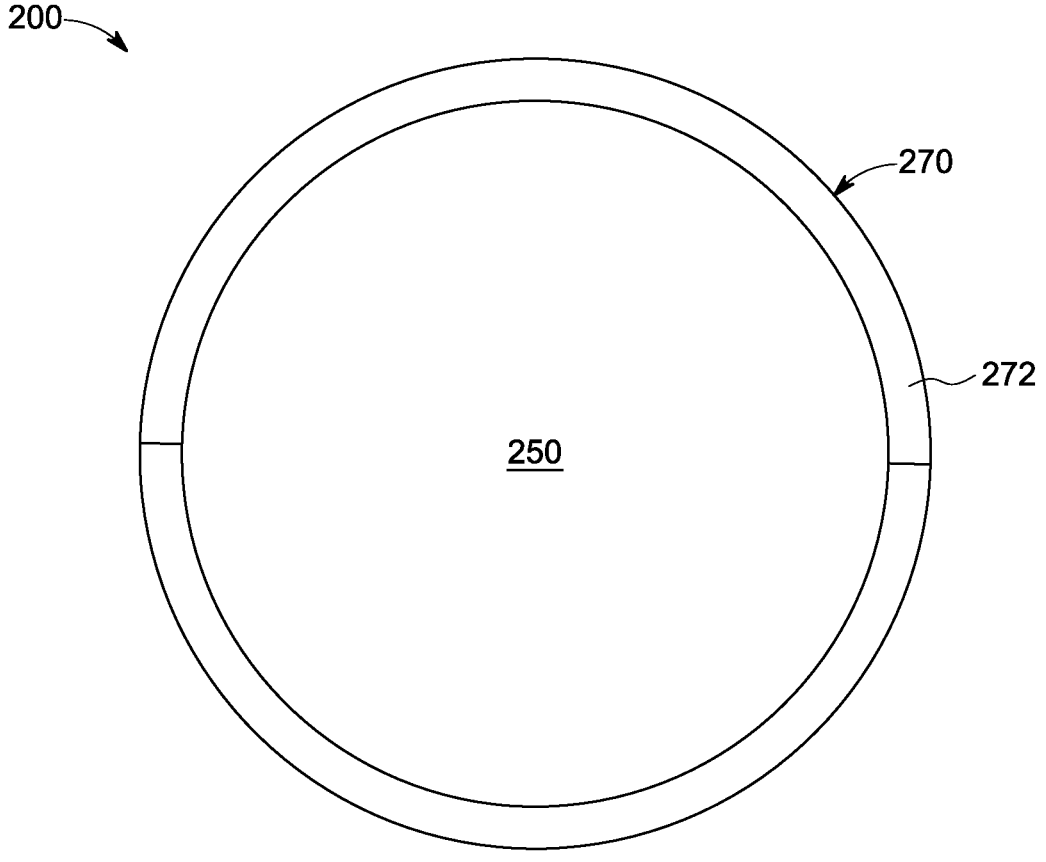
FIG. 5 is a bottom view of the toe implant of FIG. 3, according to an embodiment of the present disclosure.
Figure 6:
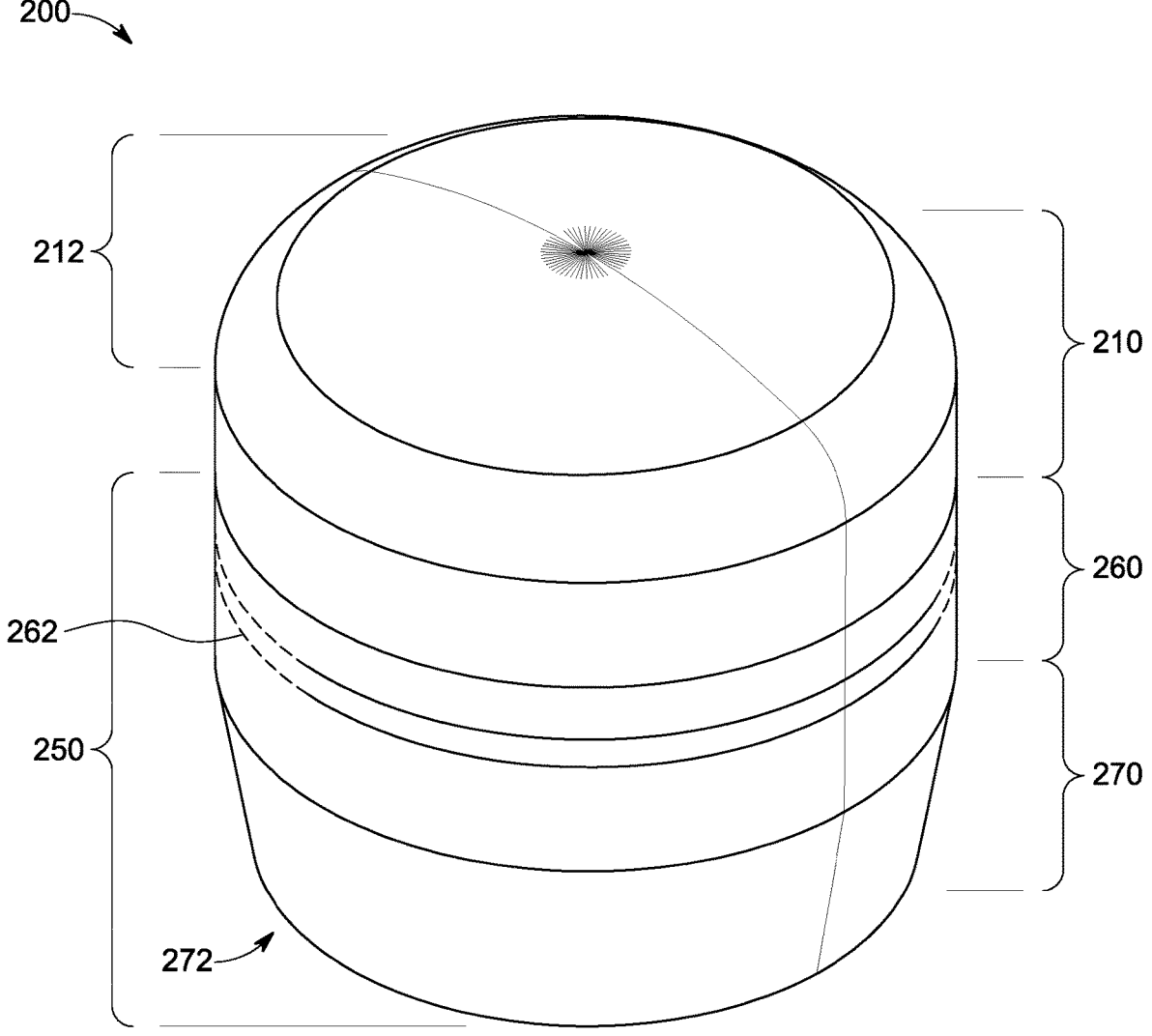
FIG. 6 is a top perspective view of the toe implant of FIG. 3, according to an embodiment of the present disclosure.
Figure 7:
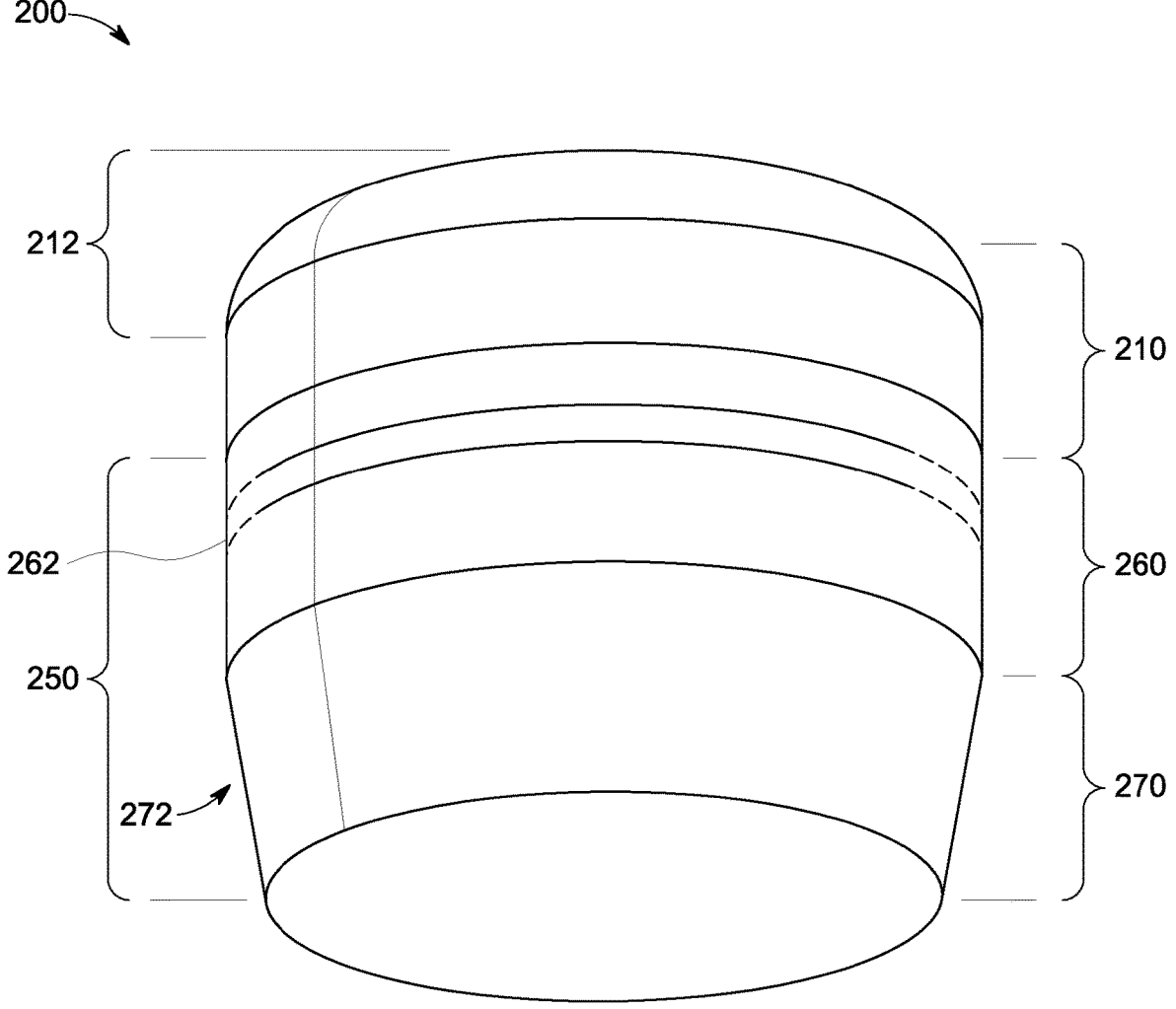
FIG. 7 is a bottom perspective view of the toe implant of FIG. 3, according to an embodiment of the present disclosure.
Figure 8:
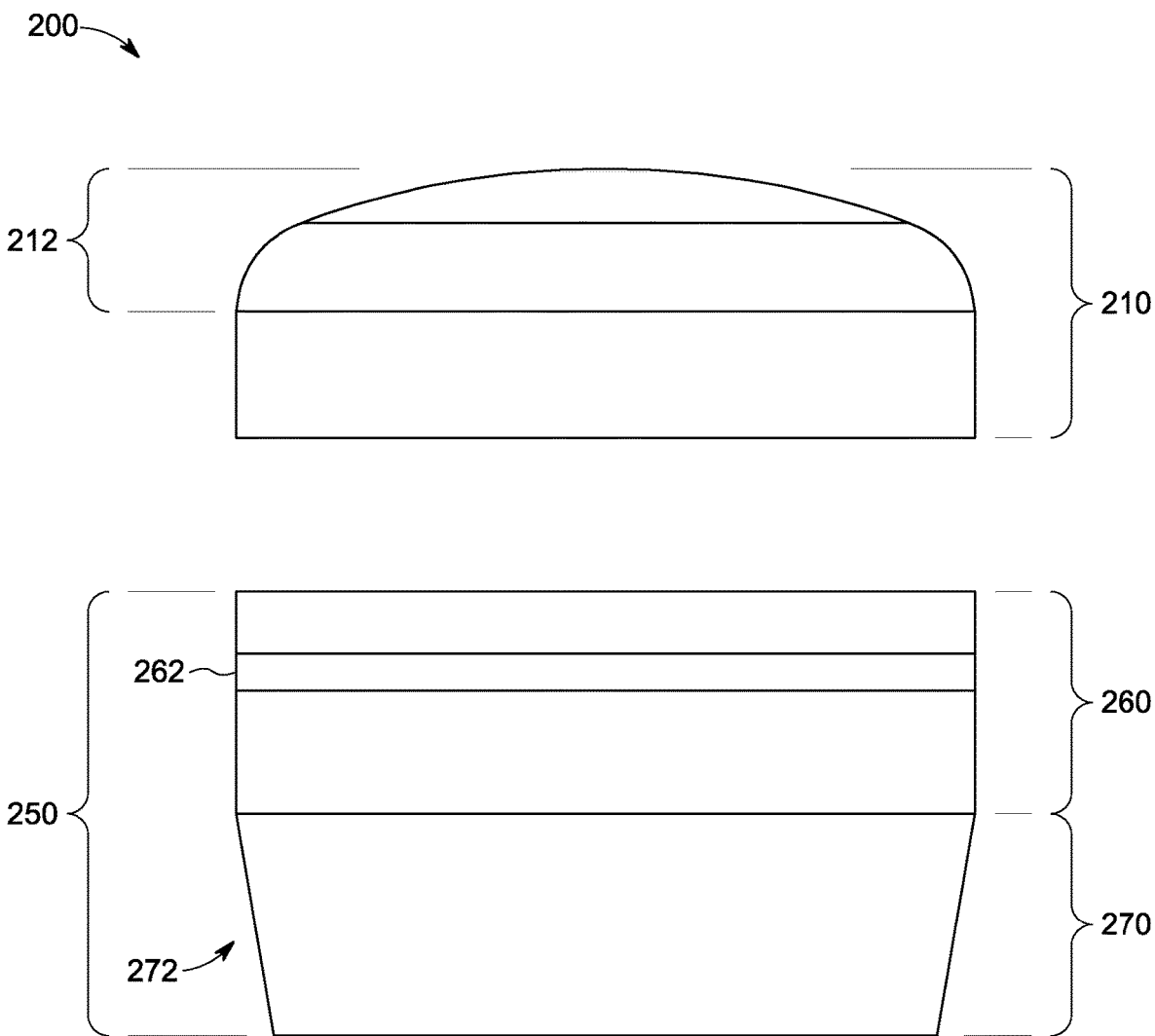
FIG. 8 is an exploded side view of the toe implant of FIG. 3, according to an embodiment of the present disclosure.
Figure 9:
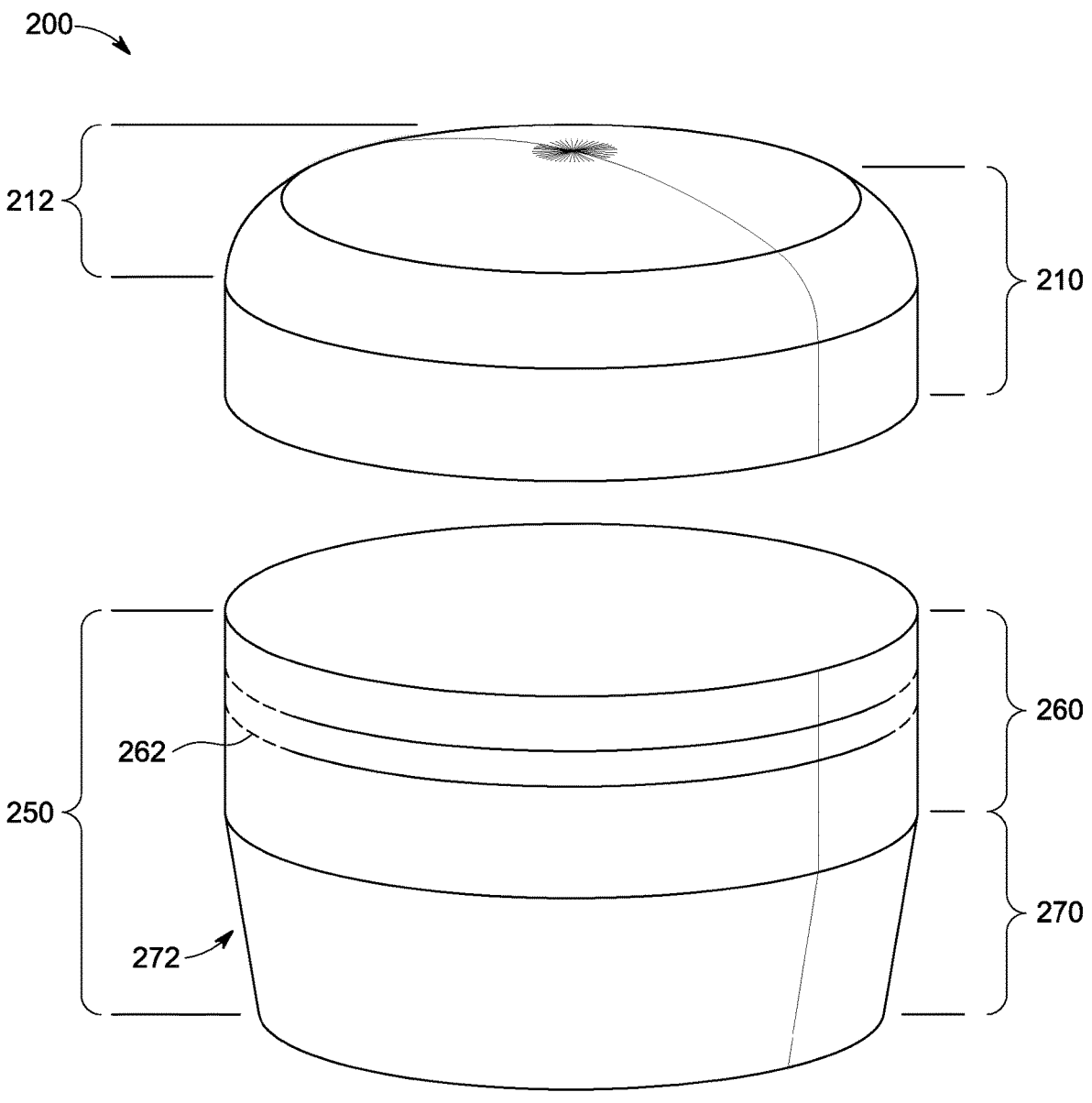
FIG. 9 is an exploded perspective view of the toe implant of FIG. 3, according to an embodiment of the present disclosure.

Generally stated, disclosed herein is a toe implant for replacing a portion of a human toe joint, as well as a related kit, surgical method, and method of manufacturing.

In this detailed description and the following claims, the words proximal, distal, anterior or plantar, posterior or dorsal, medial, lateral, superior and inferior are defined by their standard usage for indicating a particular part or portion of a patient's body, a bone, a device, or an implant according to the relative disposition of the patient or directional terms of reference. For example, "proximal" means a particular part or portion of a patient's extremity, a bone, a device or implant nearest the torso, while "distal" indicates the portion of the patient's extremity, bone, device or implant farthest from the torso. As for directional terms, "anterior" is a direction towards the front side of the body, bone, device, or implant, "posterior" means a direction towards the back side of the body, bone, device, or implant, "medial" means towards the midline of the body, "lateral" is a direction towards the sides or away from the midline of the body, "superior" means a direction above and "inferior" means a direction below another object or structure. Further, specifically in regard to the foot, the term "dorsal" refers to the top of the foot and the term "plantar" refers the bottom of the foot.

Similarly, positions or directions may be used herein with reference to anatomical structures or surfaces. For example, as the current devices, instrumentation and methods are described herein with reference to use with the bones of the foot, the bones of the foot may be used to describe the surfaces, positions, directions or orientations of the toe implant, a kit for implant installation, and a surgical method. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and surgical method, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, instrumentation and methods, and the aspects, components, features and the like thereof, described herein with respect to a left toe may be mirrored so that they likewise function with a right toe and vice versa. Further, the devices, kit, instrumentation and methods, and aspects, components, features and the like thereof, disclosed herein are described with respect to a toe for brevity purposes, but it should be understood that the devices, systems, instrumentation and methods may be used with other bones and joints of the body having similar structures.

The first metatarsophalangeal joint (MTP) is a complex joint of the foot where bones, tendons, and ligaments work together to transmit and distribute the body's weight, especially during movement. Cartilage may act as a pad and/or spacer between the first metatarsal and the proximal phalanx to facilitate movement between the bones by reducing friction and preventing the bones from grinding against each other. The present disclosure provides a solution for medical professionals to treat patients with damaged articular cartilage at the MTP joint. In particular, disclosed herein is a toe implant intended to replicate normal anatomy of a patient's metatarsal distal or phalangeal proximal head by recreating the original articular surface geometry. For instance, the bearing member of the implant may be, for example, generally convex to simulate the geometry of the metatarsal distal head or, alternatively, generally concave to simulate geometry of the phalangeal distal head. Further, the toe implant described herein may serve as a replacement pad and/or spacer by recreating the MTP joint space and replicating function of the articular cartilage.

Referring now to the drawings, wherein like reference numerals are used to indicate like or analogous components throughout the several views, and with particular reference to FIG. 1A, there is illustrated a side sectional view of an exemplary embodiment of a biocompatible toe implant 100. The toe implant 100 may include a bearing member 110 having a curved interface surface 112. Further, the toe implant 100 may include a fixation member 150 coupled to the bearing member 110. The fixation member 150 may include a first portion 160 having a non-porous barrier 162, and a tapered second portion 170. In particular, the first portion 160 may include a cylindrical shape, and the tapered second portion 170 may include a tapered cylinder shape.

Referring now to FIGS. 1A-2C, the curved interface surface 112 of the bearing member 110 of the toe implant 100 may be designed to replicate normal anatomy of a patient's toe bone such as, for example, the patient's metatarsal distal head or the patient's phalangeal proximal head. According to one embodiment, the curved interface surface 112 may be a variable curved surface, for example, or may be a constant radial surface similar to an outer portion of a sphere. If the curved interface surface 112 of the bearing member 110 is, for example, intended to replicate the patient's metatarsal distal head, the curved interface surface 112 may be configured or sized and shaped to be generally convex. The bearing member 110 may include, for example, a second surface 114 that is generally cylindrical and may be commensurate in diameter with the first portion 160 of the fixation member 150. According to one embodiment where the curved interface surface 112 includes, for example, a relatively convex surface, the curved interface surface 112 may include an upper curved edge 116 and a lower curved edge 118, where the upper curved edge 116 is a relatively gradual curve (i.e., large radius of curvature), and the lower curved edge 118 is a relatively steep curve (i.e., small radius of curvature). Further, the lower curved edge 118 may abut the upper curved edge 116 and be commensurate in diameter with the second surface 114.

For an embodiment where the curved interface surface 112 is configured or sized and shaped to replicate the surface of the patient's phalangeal proximal head, the curved interface surface 112 of the bearing member 110 may be configured or sized and shaped to be generally concave. For instance, with particular reference to FIGS. 2A-2C, the curved interface surface 112 may include a lower curved edge 118, a relatively planar surface 120, and an inner concave surface 122. The inner concave surface 122 may include a spherical radius configured or sized and shaped to engage an average metatarsal distal head size. For instance, according to one embodiment, the inner concave surface 122 may include a spherical radius of approximately 12 mm.

If the curved interface surface 112 is configured or sized and shaped to replicate the surface of the patient's phalangeal proximal head, the second surface 114 may, for example, have an approximate minimum height of 0.09 inches, measured from the center point/lowest point of the curved interface surface 112 to the start of the first portion 160 of the fixation member 150. Further, the height of the highest point around the lip or edge where the lower curved edge 118 abuts the inner concave surface 122 may include a range, for example, of approximately 0.111 in.-0.210 in. to the start of the first portion 160 of the fixation member 150. For instance, if the implant 100 is configured or sized and shaped to replicate the surface of the patient's phalangeal proximal head, the total height of the implant, which includes both the fixation member 150 and the bearing member 110, may range, for example, from about 0.428 in. to about 0.528 in., based on the fixation member 150 having an approximate height of, for example, 0.318 in.

Although not shown, various other embodiments are also contemplated herein, which may include, for example, a non-cylindrical second surface 114 depending on a particular shape of the fixation member 150. For instance, the fixation member 150, according to one embodiment, may include a cross-sectional outer surface shape that is non-cylindrical such as, for example, a polygon, triangle, square, rectangle, pentagon, hexagon, heptagon, or octagon, which may facilitate anti-rotation of the implant once implanted into the patient's bone.

Additionally, the bearing member 110 may include a hydrophilic polymer, which may, for example, include hyaluronic acid and ultrahigh molecular weight polyethylene (UHMWPE). Other embodiments may include, for example, polyurethane, polyether ether ketone (PEEK), or a hydrogel. Further examples of suitable polymeric materials are described in U.S. Pat. No. 7,662,954, issued to James, et al. entitled "Outer Layer Having Entanglement Of Hydrophobic Polymer Host And Hydrophilic Polymer Guest," which is incorporated herein by reference in its entirety. Advantageously, polymer combinations such as hyaluronic acid with UHMWPE may, for example, attract lubricating joint fluid to the bearing member 110, enabling the bearing member 110 to include self-lubricating properties. Also, other embodiments for the bearing member 110 may include, for example, metals such as cobalt chrome.

The fixation member 150 may include, according to one embodiment, at least one standard metallic biocompatible implant material such as, for example, titanium, cobalt chrome, or other acceptable stainless steels. The first portion 160 of the fixation member 150 may include various layers. For instance, the first portion 160 may include, for example, a first section 164 positioned between the bearing member 110 and the non-porous barrier 162. In one embodiment, the first section 164 may include, for example, a titanium-based porous material, which may include at least one void 166 capable of receiving the hydrophilic polymer during the manufacturing process. The first portion 160 may also include, for example, a second section that includes the non-porous barrier 162. Further, the first portion 160 may also include a third section 168 positioned between the non-porous barrier 162 and the tapered second portion 170. The third section 168 may also include, for example, additional titanium-based porous material, which may also include at least one void 166 capable of receiving bone ingrowth after implantation. The at least one void 166 may, for example, include an approximate average pore size of 523 microns and include an average interconnection size of approximately 229 microns. Further, the overall porosity of the first section 164, the third section 168 and the tapered second portion 170 may be, for example, approximately 60%, Further, the tapered second portion 170 of the toe implant 100 may also include an angular surface 172 capable of preventing subsidence of the toe implant 100 into a patient's metatarsal bone. For instance, the angular surface 172 may be angled such that the tapered second portion 170 includes, for example, a first diameter $D_1$ at the top 174 of the tapered second portion 170, and a second diameter $D_2$ at the bottom 176 of the tapered second portion 170. Further, the second diameter $D_2$ may be less than the first diameter $D_1$ such that $D_2 < D_1$. The angular surface 172 may include, for example, any angle capable of providing adequate resistance to prevent the implant 100 from subsiding into the patient's resected metatarsal head post-implantation. In particular, the angular surface 172 may be pressed into a patient's resected metatarsal such that the angular surface 172 engages the inner walls of the metatarsal bone to better secure the implant 100 to the metatarsal head. For instance, according to one embodiment, the angular surface 172 may be angled, for example, approximately 20 degrees inward from the first diameter $D_1$ to the second diameter $D_2$. In other embodiments, the angular surface 172 may include an angle that is, for example, larger or smaller depending on the diameter size of the fixation member 150. In various embodiments, the tapered second portion 170 may adjoin the non-porous barrier 162, such that the entire bottom portion of the implant 100 includes an angular surface 172. In other embodiments, the fixation member 150 may be comprised of a biocompatible non-metallic polymer such as, for example, polyether ether ketone (PEEK).

The fixation member 150 may include a total height $H_T$ that is a summation of a height $H_1$ of the first portion 160 and a height $H_2$ of the tapered second portion 170 such that $H_1+H_2=H_T$. Various ratios and approximate distributions of the aggregate height of the cylindrical member 160 relative to the tapered second portion 170, may be possible including, for example, $H_1 \approx 1.0$ to $3.0 \times H_2$, or more particularly $H_1 \approx 1.3$ to $1.7 \times H_2$.

In one embodiment, the fixation member 150 may, for example, be non-porous and have a surface treatment for the angular surface 172 and/or other portions of the implant 100 to interact with the inner walls of the resected bone of the metatarsal head. The surface treatment may include, for example, a porous coating such as a hydroxyapatite (HA) coating, titanium plasma spray, or grit blasting, which may allow for a higher coefficient of friction to better fix the implant 100 in the resected metatarsal head and promote bone in growth. Further, the implant 100 may be affixed to the metatarsal distal head or phalangeal proximal head with, for example, a pin, stem, screw, bone cement, or a combination thereof in order to prevent movement, prevent the implant 100 from sliding out of the resected bone of either the metatarsal distal head or phalangeal proximal head, and facilitate bone in growth.

The toe implant 100 may be designed in multiple sizes to allow selection by a medical professional based on the width and/or depth of the particular metatarsal bone or phalangeal bone being treated. According to one embodiment, the total diameter of the implant 100 may be commensurate with the diameter of the first portion 160 of the implant 100. For an implant 100 that may be configured or sized and shaped to replicate the metatarsal distal head, the total diameter may be selected from a plurality of differently sizes based on normal surface anatomy of a patient's metatarsal distal head. Sizes may range, for example, between 6 mm and 14 mm, with measurements of example sizes 6 mm, 8 mm, 10 mm, 12 mm, and 14 mm shown in Table 1 below.

TABLE 1

|  | Implant Diameter | $D_1$ (inches) | $D_2$ (inches) | $H_I$ (inches) |
|---|---|---|---|---|
| a) | 6 mm | 0.2367 | 0.195 | 0.411 |
| b) | 8 mm | 0.3156 | 0.274 | 0.482 |
| c) | 10 mm | 0.3912 | 0.350 | 0.498 |
| d) | 12 mm | 0.4723 | 0.431 | 0.519 |
| e) | 14 mm | 0.5512 | 0.510 | 0.544 |

As mentioned above, and with reference to Table 1, diameter $D_1$ includes an approximate diameter at the top 174 of the tapered second portion 170, as well as the diameter of the first portion 160 of the fixation member 150, and diameter $D_2$ includes an approximate diameter at the bottom 176 of the tapered second portion 170 of the implant 100. Further, height $H_1$ represents the full height of the implant 100 from the center of the bearing member 110 at the highest point of the upper curved edge 116 to the bottom 176 of the tapered second portion 170.

For an implant 100 configured or sized and shaped to replicate the phalangeal proximal head, the total diameter may be selected from a plurality of different sizes based on normal surface anatomy of a patient's phalangeal proximal head. Example sizes may range between 10 mm and 20 mm, with measurements of example sizes 10 mm and 20 mm shown in Table 2 below.

TABLE 2

|  | Implant Diameter | $D_1$ (inches) | $H_I$ (inches) | $H_{BM}$ (inches) |
|---|---|---|---|---|
| a) | 10 mm | 0.392 | 0.429 | 0.111 |
| b) | 20 mm | 0.787 | 0.528 | 0.210 |

With reference to Table 2, and as stated above, diameter $D_1$ includes an approximate diameter at the top 174 of the tapered second portion 170, as well as the diameter of the first portion 160 of the fixation member 150. Further, height $H_1$ represents the full height of the implant 100 from the highest point around the lip or edge where the lower curved edge 118 abuts the inner concave surface 122 to the bottom 176 of the tapered second portion 170. Additionally, height $H_{BM}$ represents the height of the bearing member 110 measured from the start of the first portion 160 of the fixation member 150 to the highest point around the lip or edge where the lower curved edge 118 abuts the inner concave surface 122.

In FIGS. 3-9, an exemplary implant 200 is shown that is configured or sized and shaped to replicate the metatarsal distal head. In particular, an exemplary implant 200 having a diameter of 10 mm is illustrated. However, it will be appreciated that other sizes such as, for example, the implant diameters of Table 1 or Table 2, and/or shapes may be acceptable to cover different sized and/or shaped anatomic metatarsal heads. The implant 200 may be a one-piece, integral, or monolithic structure. Further, the implant 200 may include a bearing member 210 having a curved interface surface 212 and a fixation member 250 coupled to the bearing member 210. The fixation member 250 may include, for example, a first portion 260 that includes a non-porous barrier 262, and a tapered second portion 270 that includes an angular surface 272. Further, the non-porous barrier 262 may bisect the fixation member 250 into at least two sections. For instance, the non-porous barrier 262 may, for example, bisect the first portion 260 into two sections or may, for example, separate the first portion 260 from the tapered second portion 270. The curved interface surface 212 may include at least one of a convex surface and a concave surface (see FIGS. 2A-2C), depending on whether the implant 200 is to be inserted into the patient's metatarsal distal head or phalangeal proximal head.

FIGS. 10-18 illustrate a process for treating articular cartilage damage of the MTP joint, with particular examples being provided showing insertion of the implant 100 into the metatarsal distal head. Although not shown, a similar approach to the following description may also be used on the phalangeal proximal head.

Figure 10:
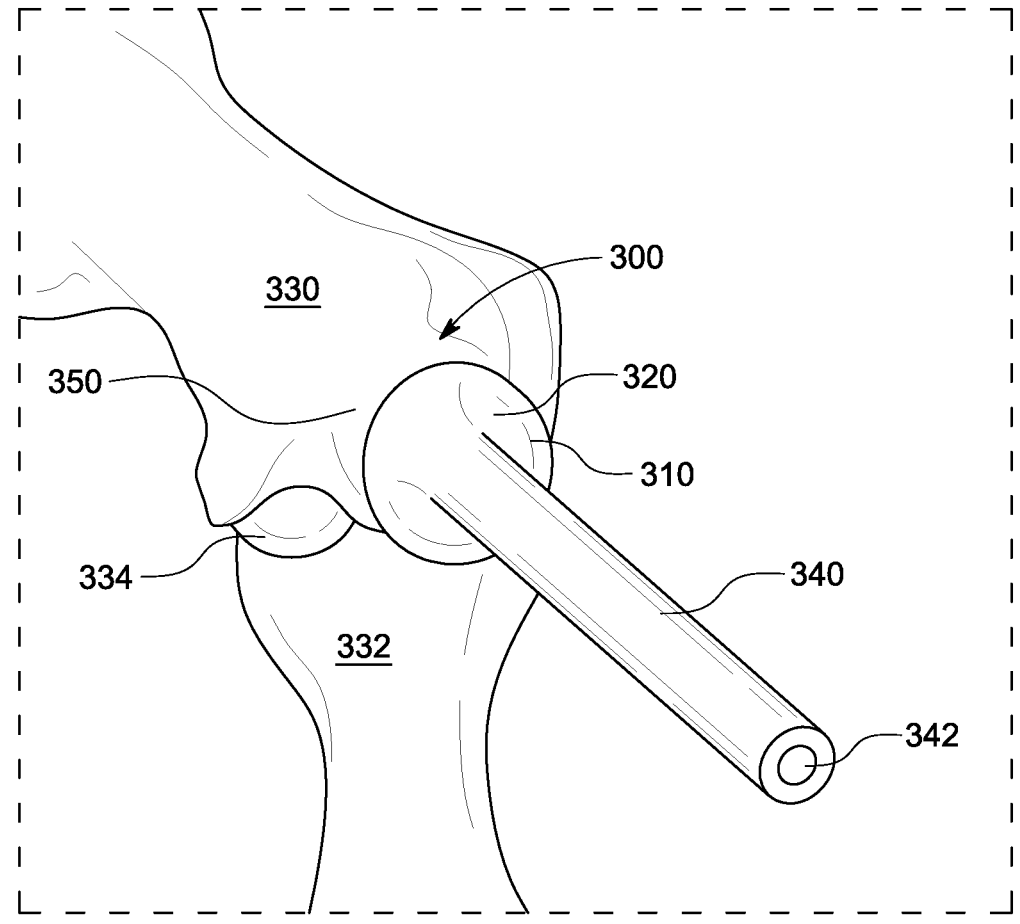
FIG. 10 illustrates an exposed metatarsal head being sized for inserting an exemplary trial toe implant of an exemplary guide, according to an embodiment of the present disclosure.

FIG. 10 illustrates an exposed metatarsal head 330 being sized using an exemplary trial toe implant 300, according to an embodiment of the present disclosure. During insertion, the proximal phalanx 332 may be positioned downward below the sesamoid bone 334 to expose the metatarsal head 330. Disclosed herein, according to one embodiment is a kit, which includes an exemplary guide 300 that includes a trial toe implant 320 attached to a shaft 340, where the shaft 340 is adjoined to the bearing member 310 of the trial toe implant 320. The fixation member 350 of the trial toe implant 320 may be aligned to the metatarsal head 330 to determine a proper size for the implant 100 (see FIGS. 17-18) to be later inserted into the metatarsal head 330. Additionally, the shaft 340 of the guide 300 may include an engagement slot 342 through which a positioning device 344 (see FIG. 11) may be inserted for aligning a reamer 346 (see FIG. 12).

Figure 11:
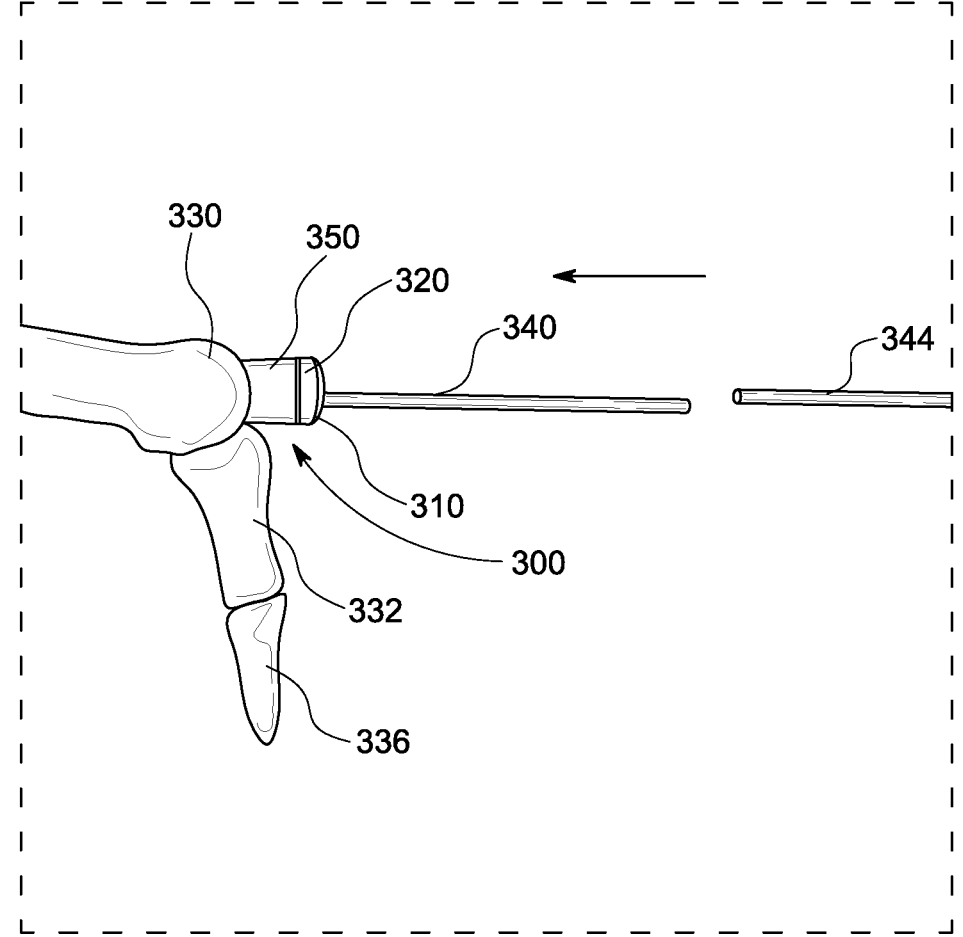
FIG. 11 is a lateral view illustrating the exposed metatarsal head and the exemplary trial toe implant of the exemplary guide of FIG. 10, wherein an exemplary positioning device may be inserted through the exemplary guide, according to an embodiment of the present disclosure.

Referring now to FIG. 11, the kit may include a positioning device 344, such as, for example, a pin, configured to engage the engagement slot 342 (see FIG. 10) of the shaft 340. The positioning device 344 may be inserted through the engagement slot 342 (see FIG. 10) of the shaft 340 to provide proper positioning of the reamer 346 (see FIG. 12) relative to the metatarsal head 330. As shown, the proximal phalanx 332 and distal phalanx 336 may be positioned downward during this process to provide access to the metatarsal head 330. Further, the bearing member 310 of the trial toe implant 320 may be facing the shaft 340 and the fixation member 350 may be aligned to the metatarsal head 330.

Figure 12:
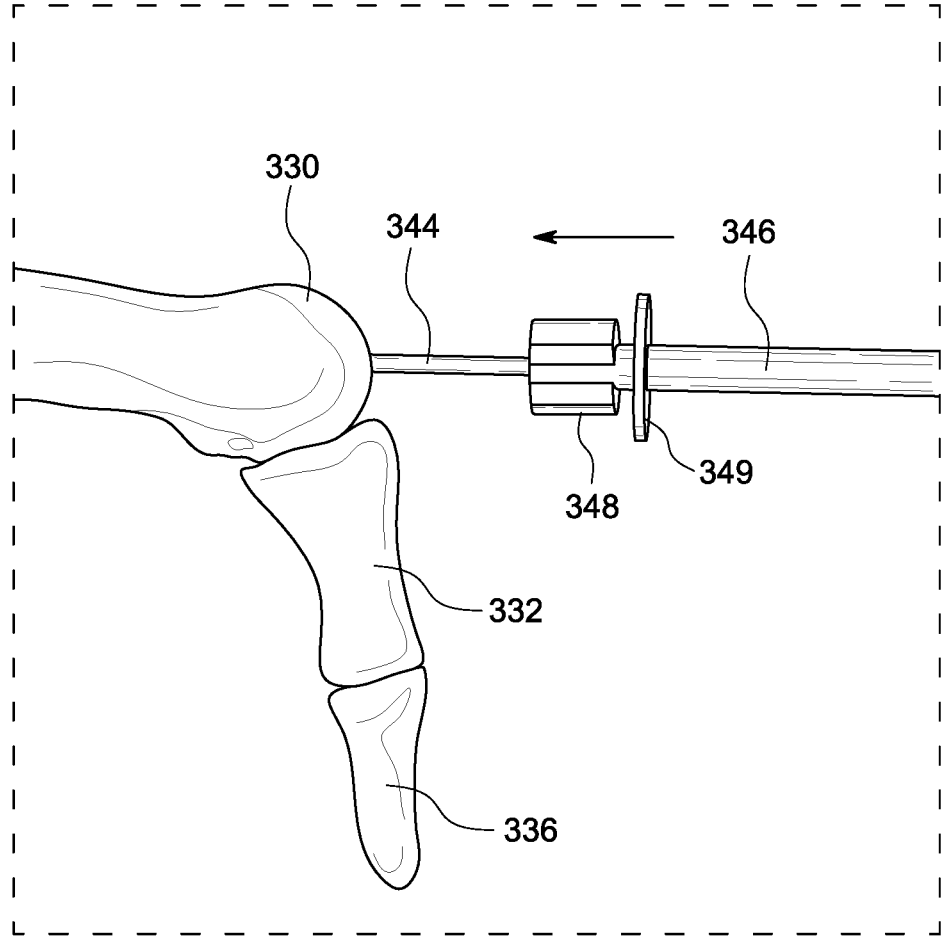
FIG. 12 is a lateral view illustrating the exposed metatarsal head and exemplary positioning device of FIG. 11, wherein the exemplary positioning device is engaging a reamer for reaming the metatarsal head, according to an embodiment of the present disclosure.

Referring now to FIG. 12, the kit may include a reamer 346 that includes at least one cutting flute 348 or other cutting apparatus for preparing the metatarsal head 330 for implantation. The reamer 346 and at least one cutting flute 348 may be sized (see FIGS. 10-11) to correspond to an appropriate diameter and radius, respectively, of the implant 100 (see FIGS. 17-18) to be inserted. The at least one cutting flute 348 may be configured to resect, during rotation of the reamer 346, a portion of the metatarsal head 330. The reamer 346 may be designed to fit various sized patient anatomies that may be encountered. For example, various reamers 346 may be designed and adapted for multiple radii of curvature, width, and depth options to allow for providing the best fit for a given patient's anatomy. The reamer 346 may also include variations of diameter along the length of the flute 348 to provide for a changing diameter along the inner wall of the resected portion of the metatarsal head 330, which may, for example, correspond to a tapered portion of the fixation member 350 (see FIGS. 10-11) of the trial toe implant 320 (see FIGS. 10-11). The reamer 346 may also include a barrier 349 to, for example, provide an appropriate depth for which the metatarsal head 330 is to be reamed and/or prevent the reamer 346 from resecting too far into the metatarsal head 330. The reamer 346 may include an engagement slot configured to engage the positioning device 344 in order to provide proper alignment for the reamer 346 relative to the metatarsal head 330. During this process, the proximal phalanx 332 and distal phalanx 336 may remain positioned downward to maintain access to the metatarsal head 330.

Figure 13:
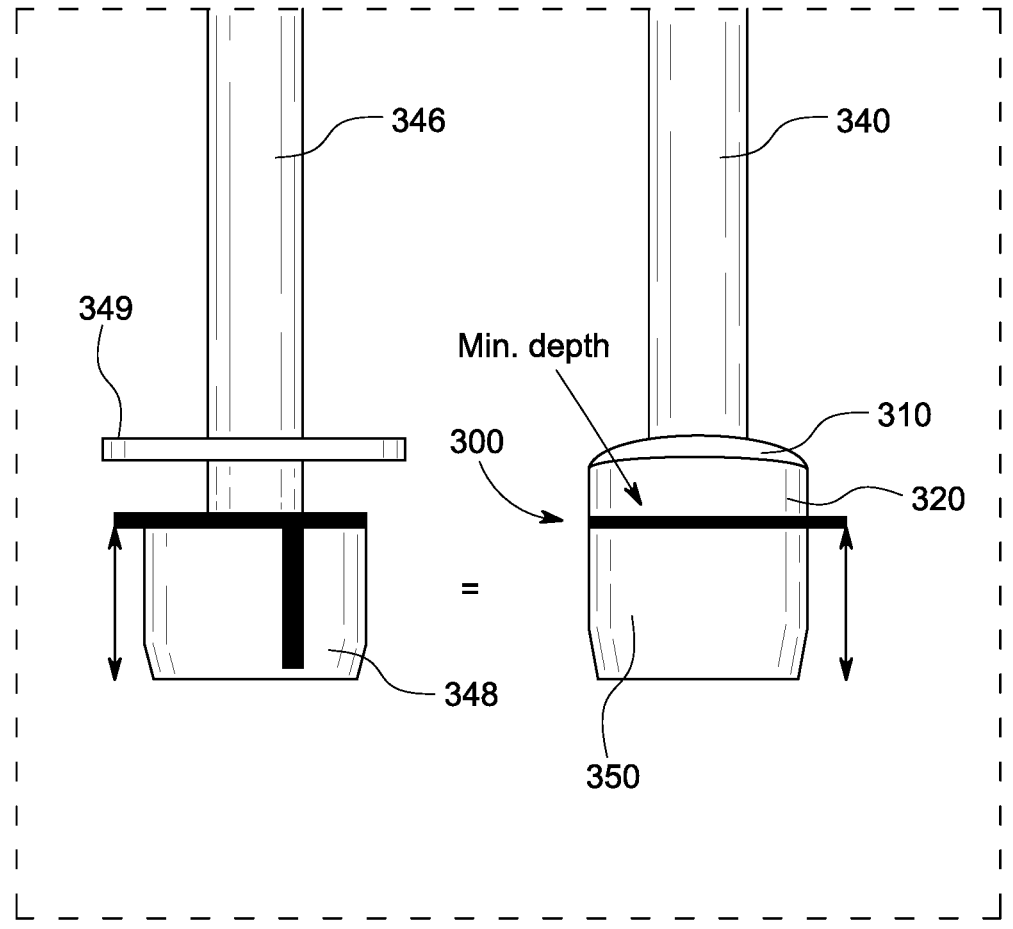
FIG. 13 illustrates the exemplary reamer of FIG. 12 and the exemplary guide of FIG. 10, according to an embodiment of the present disclosure.

FIG. 13 illustrates the exemplary reamer 346 of FIG. 12 and the exemplary guide 300 of FIGS. 10-11. According to one embodiment, the reamer 346 may, for example, have at least one cutting flute 348 of a length corresponding to a minimum insertion depth of the trial toe implant 320 of the guide 300. In particular, the flute 348 length may correspond to a length of the fixation member 350 of the trial toe implant 320. In another example, the flute 348 length may correspond to a length of the fixation member 350 in addition to a portion of the bearing member 310. Various other flute 348 lengths may be possible depending on the desired insertion depth of the implant 100 (see FIGS. 17-18) to be inserted. According to one embodiment, the barrier 349 may, for example, correspond to the height of the bearing member 310 of the trial toe implant 320, which may enable the bearing member 310 of the implant 100 (see FIGS. 17-18) to be inserted to sit relatively flush with the metatarsal head 330 (see FIGS. 10-12). For other implementations, the bearing member 310 may, for example, be slightly depressed or proud relative to the metatarsal head 330 (see FIGS. 10-12) depending on the patient's anatomy. In particular, it may be desirous that the bearing member 310 of the trial toe implant 320 be positioned above the surface of the metatarsal head 330 (see FIGS. 10-12) such that the bearing member 310 positioning corresponds to an amount of cartilage between the metatarsal head 330 and proximal phalanx 332 (see FIGS. 10-12). For example, according to one embodiment, the flute 348 length may correspond to a desired reamed depth into the metatarsal head 330 (see FIGS. 10-12), and the barrier 349 may represent a point that is approximately 5 mm higher than the height of the fixation member 350 of the trial toe implant 320. Further, the flute 348 length on the reamer 346 may, for example, be the same height as the minimum depth to ensure that the fixation member 350 is adequately inserted into the bone.

In some embodiments, for each reamer 346 and/or at least one cutting flute 348 there would, for example, be a corresponding implant radius. Additionally, the kit of the present disclosure may include reusable tools or single use tools. In other embodiments, a reamer 346 and/or at least one flute 348 may be operably adjustable, e.g., to adjust the angle and/or the depth of the cut to be made, so as to be used with any number of implants that may be selected.

Figure 14:
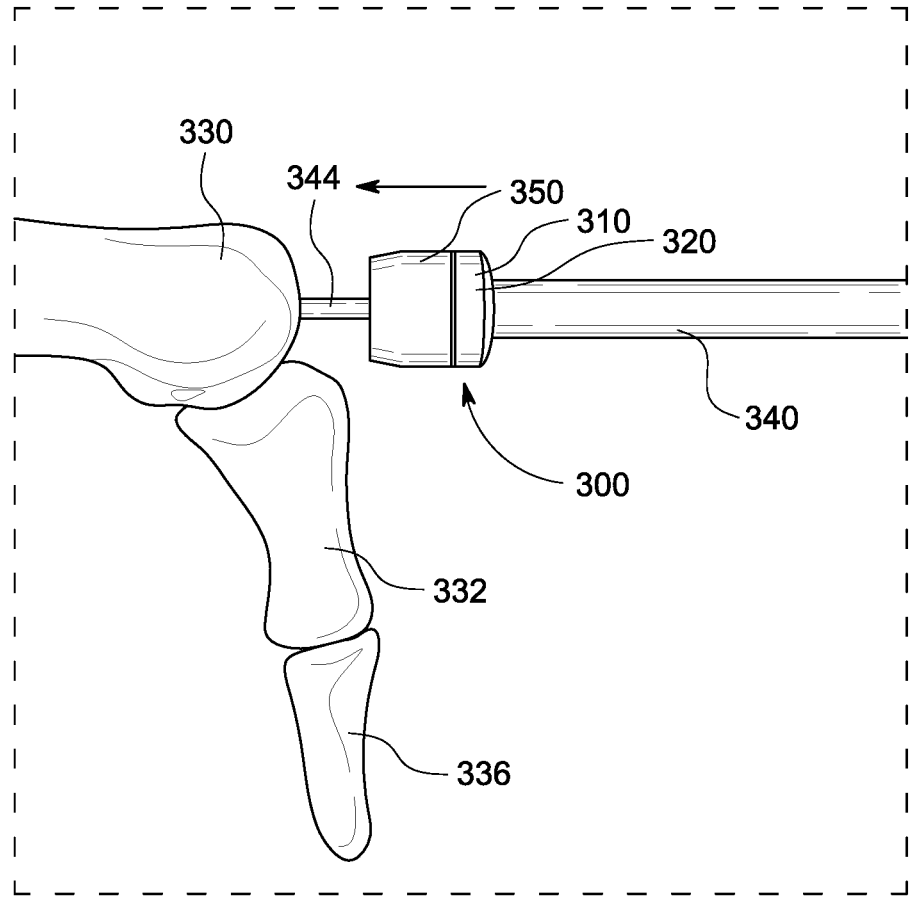
FIG. 14 is a lateral view showing the exemplary positioning device of FIG. 11 being used in conjunction with the exemplary guide of FIG. 10, according to an embodiment of the present disclosure.

FIG. 14 illustrates the exemplary guide 300 with the bearing member 310 of the trial toe implant 320 and the fixation member 350 of the trial toe implant 320 engaging the positioning device 344. The positioning device 344 may be inserted into a portion of the patient's metatarsal head 330, which facilitates aligning the trial toe implant 300 for insertion to determine whether the metatarsal head 330 has been reamed to an adequate depth. As stated previously, the proximal phalanx 332 and the distal phalanx 336 remain positioned downward to provide access to the metatarsal head 330.

Figure 15:
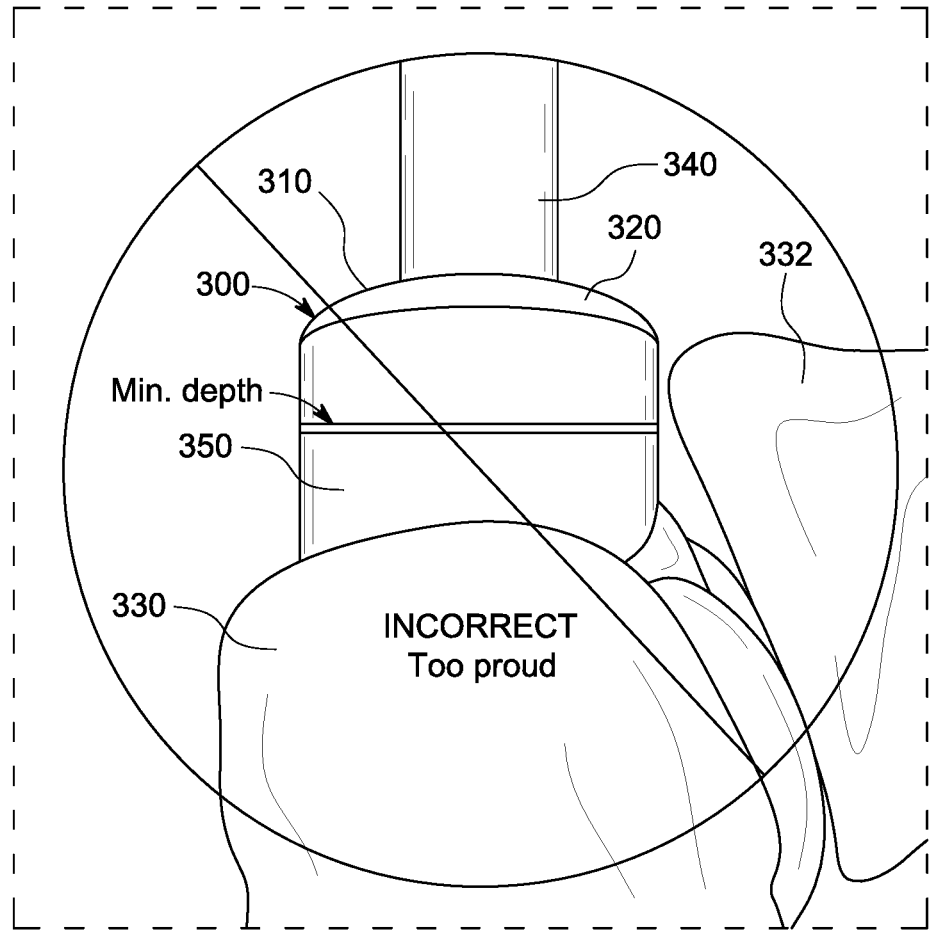
FIG. 15 illustrates the exemplary trial toe implant of the guide of FIG. 10 that is inserted to an improper depth, according to an embodiment of the present disclosure.
Figure 16:
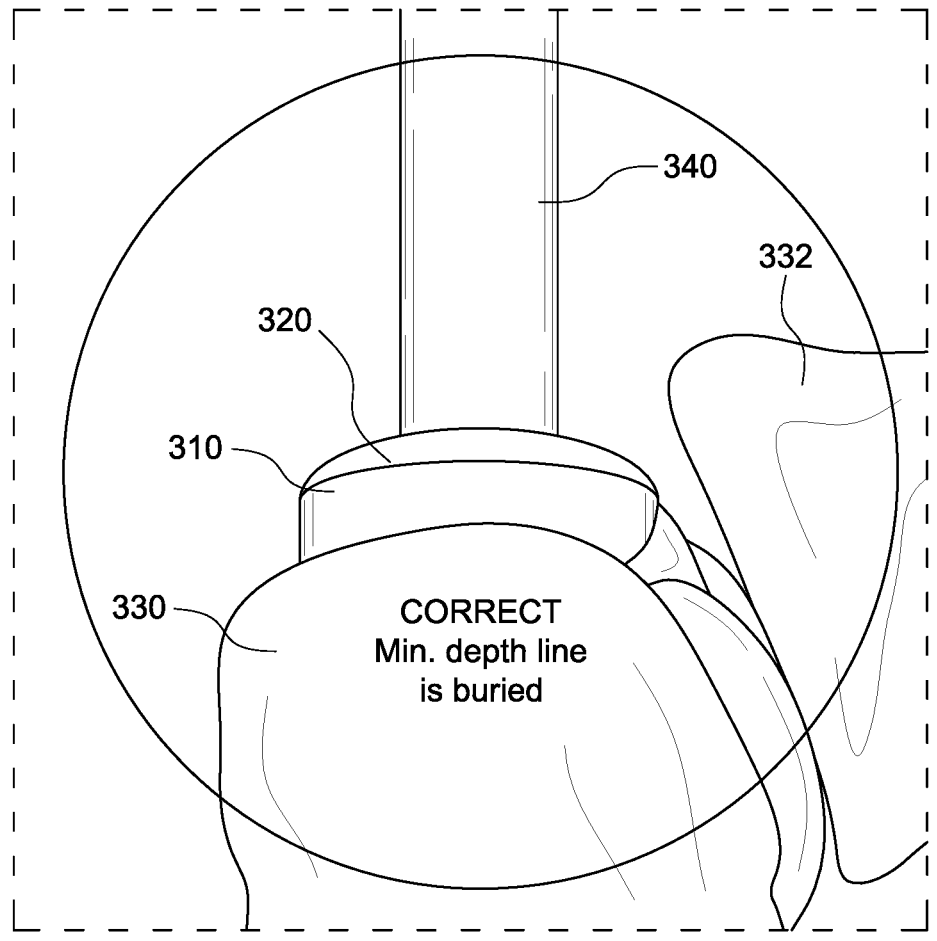
FIG. 16 illustrates the exemplary trial toe implant of FIG. 10 that is inserted to a proper depth, according to an embodiment of the present disclosure.

FIGS. 15 and 16 illustrate the exemplary trial toe implant 300 during insertion into the patient's metatarsal head 330. In particular, FIG. 15 shows a partial insertion of the trial toe implant 320 of the guide 300, where the trial toe implant 320 is not fully and/or properly inserted. For instance, the trial toe implant 320 may, for example, not be sufficiently inserted due to the resected metatarsal head 330 not being sufficiently resected to a depth that would correspond to the minimum depth required for the entirety of the fixation member 350 to be fully inserted into the metatarsal head 330. For example, as shown in FIG. 16, only the bearing member 310 of the trial toe implant 320 is visible above the metatarsal head 330, and the trial toe implant 320 is inserted the minimum depth.

Figure 17:
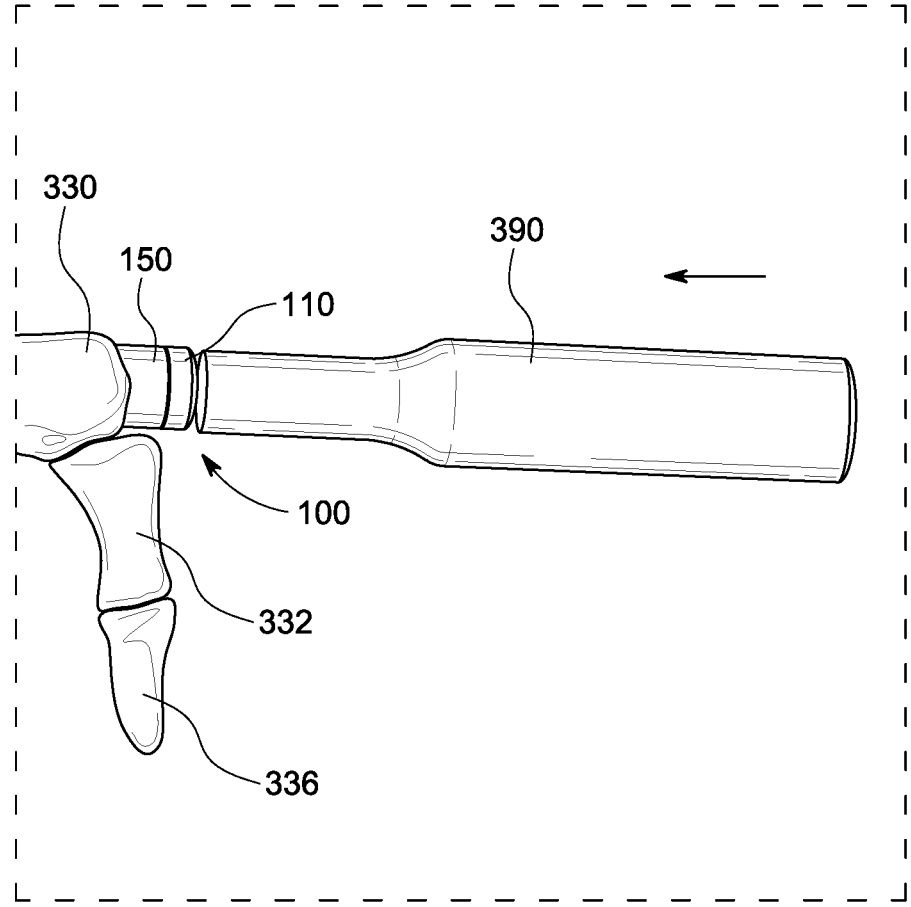
FIG. 17 is a lateral view of a tamper being used to tamp into position the exemplary toe implant of FIGS. 1A-2C, according to an embodiment of the present disclosure.

The kit further includes a tamper 390, as seen in FIG. 17, for tamping down the implant 100 into the patient's metatarsal head 330. The portion of the tamper 390 configured to be in contact with the bearing member 110 of the implant 100 may correspond in size to the diameter of the implant 100 such that only the implant 100 is contacted during tamping. The tamper 390 may facilitate inserting the implant 100 a sufficient depth such that the fixation member 150 of the implant 100 is fully seated into the patient's metatarsal head 330. During this process, the proximal phalanx 332 and the distal phalanx 336 may remain positioned downward to provide access to the metatarsal head 330.

Figure 18:
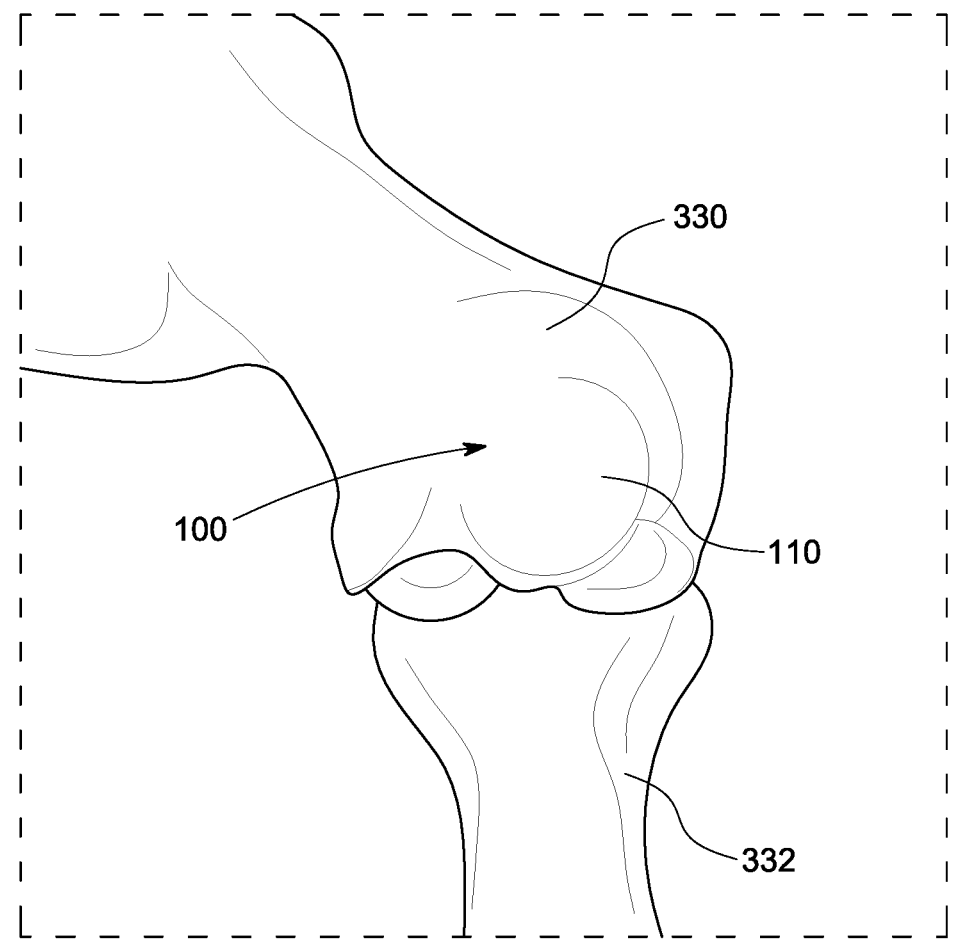
FIG. 18 illustrates the exemplary toe implant of FIGS. 1A-2C post-implantation, according to an embodiment of the present disclosure.

FIG. 18 illustrates the implant 100 post-implantation, according to an aspect of the present invention. The implant 100 may be, for example, inserted into the metatarsal head 330 such that only the bearing member 110 is visible and/or capable of contacting the proximal phalanx 332.

Also disclosed herein is a surgical method. Referring now to FIG. 19, a flowchart of a surgical method 400 is illustrated. The surgical method 400 may include, for example, a process of exposing a patient's metatarsophalangeal joint 402. Additionally, the method 400 may include sizing at least one of the patient's metatarsal distal head or phalangeal proximal head 404 and positioning a trial toe implant and guide 406. Further, a positioning device may be fixated into at least one of the patient's metatarsal distal head or phalangeal proximal head 408 via the guide's engagement slot. The trial toe implant and guide may then be removed 410, and a reamer may be positioned over the positioning device 412 via the reamer's engagement slot. The method 400 may also include reaming the at least one of the patient's metatarsal head or phalangeal proximal head 414 to a predetermined depth and tamping the implant into the at least one of the patient's resected metatarsal distal head or phalangeal proximal head 416. The method may also include closing the patient's incision 418.

Figure 20:
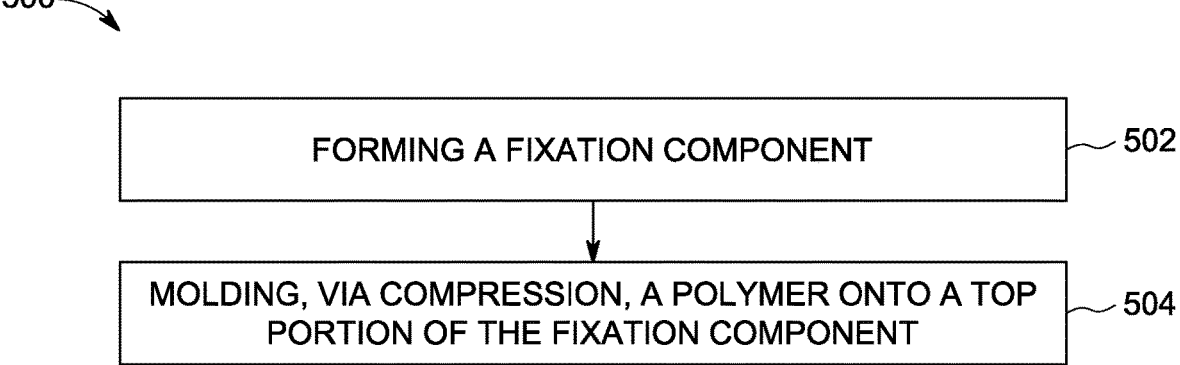
FIG. 20 is a flowchart of a method of manufacturing the exemplary implant, according to an embodiment of the present disclosure.

FIG. 20 illustrates a flowchart of a method of manufacturing 500, according to an embodiment of the present disclosure. For instance, the method of manufacturing 500 may include, for example, forming a fixation member 502 and molding, via compression, a polymer onto a top portion of the fixation member 504. Formation of the fixation member 502 may include, for example, layering a plurality of sheets of titanium-based material to a desired height. In other embodiments, the plurality of sheets may include tantalum-based structures, or other suitable material or materials. At least one sheet of the plurality of sheets may include, for example, a porous material. According to various embodiments, the porous portions of the fixation member (see, for example, FIGS. 1A-9) may be sprayed or sinter-coated. The porous material may include a top portion of the fixation member and a bottom portion of the fixation member, and at least one sheet of the plurality of sheets includes a non-porous material, where the non-porous material bisects the top portion of the fixation member from the bottom portion of the fixation member. Formation of the fixation member 502 may also include cutting at least one diameter of the fixation member from the plurality of sheets and cutting an angular surface into a bottom segment of the bottom portion of the fixation member.

Molding, via a compression process, the polymer onto a top portion of the fixation member 504 may also include, for example, applying heat to the polymer and applying pressure to the polymer. This method of manufacture 500 may enable the polymer to flow in a controlled manner into any voids in the porous material of the top portion of the fixation member, and the polymer may stop flowing upon reaching the non-porous material.

As may be recognized by those of ordinary skill in the art based on the teachings herein, numerous changes and modifications may be made to the above-described and other embodiments of the present invention without departing from the scope of the invention. The implants, screws, and other components of the devices and/or apparatus as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and apparatus may include more or fewer components or features than the embodiments as described and illustrated herein. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general apparatus operation. Modifications and alterations will occur to others upon a reading and understanding of the preceding detailed description. It is intended that the invention be construed as including all such modifications and alterations.

What is claimed is:

1. A kit, comprising:
    a toe implant, comprising:
        a bearing member, having:
            a curved interface surface, and
        a fixation member coupled to the bearing member, the fixation member comprising:
            a first portion, comprising:
                a non-porous barrier, and
            a tapered second portion;
    a guide comprising:
        a trial toe implant,
        a shaft, and
        an engagement slot traversing the trial toe implant and the shaft;
    a positioning device configured to engage the engagement slot of the guide;
    a reamer comprising:
        at least one cutting flute, and
        a reamer engagement slot configured to engage the positioning device; and
    a tamper.

2. The kit of claim 1, wherein a length of the at least one cutting flute is equal to a length of the fixation member.

3. The kit of claim 1, wherein a length of the at least one cutting flute corresponds to a minimum insertion depth of a trial toe implant.

4. The kit of claim 1, wherein the tamper comprises a portion configured to contact the bearing member of the toe implant.

5. The kit of claim 4, wherein the portion configured to contact the bearing member of the toe implant comprises at least one of a convex surface and a concave surface.

\* \* \* \* \*